(12) United States Patent
Bueno et al.

(10) Patent No.: US 12,023,108 B2
(45) Date of Patent: *Jul. 2, 2024

(54) SYSTEM AND METHOD FOR A TISSUE RESECTION MARGIN MEASUREMENT DEVICE

(71) Applicant: THE BRIGHAM AND WOMEN'S HOSPITAL, INC., Boston, MA (US)

(72) Inventors: Raphael Bueno, Brookline, MA (US); Jayender Jagadeesan, Boston, MA (US); Ferenc A. Jolesz, Brookline, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 367 days.

This patent is subject to a terminal disclaimer.

(21) Appl. No.: 17/365,668

(22) Filed: Jul. 1, 2021

(65) Prior Publication Data

US 2022/0168046 A1 Jun. 2, 2022

Related U.S. Application Data

(63) Continuation of application No. 15/068,119, filed on Mar. 11, 2016, now Pat. No. 11,058,494, which is a (Continued)

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/066* (2013.01); *A61B 17/068* (2013.01);
(Continued)

(58) Field of Classification Search
CPC .. A61B 34/20; A61B 2034/2046–2074; A61B 34/25; A61B 2034/252–258; A61B 90/37–39; A61B 2090/3904–3995
See application file for complete search history.

(56) References Cited

U.S. PATENT DOCUMENTS

| 5,800,445 A | 9/1998 | Ratcliff et al. |
| 6,056,700 A | 5/2000 | Burney et al. |
(Continued)

FOREIGN PATENT DOCUMENTS

| CN | 101320526 A | 12/2008 |
| CN | 103908344 A | 7/2014 |
(Continued)

OTHER PUBLICATIONS

Communication pursuant to Article 94(3) EPC in EP Application No. 17764248.5 dated Feb. 17, 2023 (16 pages).
(Continued)

*Primary Examiner* — Carolyn A Pehlke
(74) *Attorney, Agent, or Firm* — Quarles & Brady LLP

(57) ABSTRACT

Embodiments of the invention provide a system and method for resecting a tissue mass. The system for resecting a tissue mass includes a surgical instrument and a first sensor for measuring a signal corresponding to the position and orientation of the tissue mass. The first sensor is dimensioned to fit insider or next to the tissue mass. The system also includes a second sensor attached to the surgical instrument configured to measure the position and orientation of the surgical instrument. The second sensor is configured to receive the signal from the first sensor. A controller is in communication with the first sensor and/or the second sensor, and the controller executes a stored program to calculate a distance between the first sensor and the second sensor. Accordingly, visual, auditory, haptic or other feed-
(Continued)

back is provided to the clinician to guide the surgical instrument to the surgical margin.

22 Claims, 6 Drawing Sheets

Related U.S. Application Data continuation-in-part of application No. PCT/US2014/054310, filed on Sep. 5, 2014.

(60) Provisional application No. 61/874,675, filed on Sep. 6, 2013.

(51) Int. Cl.
| | | |
|---|---|---|
| A61B 17/00 | (2006.01) | |
| A61B 17/068 | (2006.01) | |
| A61B 17/32 | (2006.01) | |
| A61B 17/3205 | (2006.01) | |
| A61B 17/50 | (2006.01) | |
| A61B 18/14 | (2006.01) | |
| A61B 34/10 | (2016.01) | |
| A61B 90/00 | (2016.01) | |
| A61B 18/00 | (2006.01) | |

(52) U.S. Cl.
CPC .. *A61B 17/320016* (2013.01); *A61B 17/3205* (2013.01); *A61B 17/50* (2013.01); *A61B 18/1477* (2013.01); *A61B 90/361* (2016.02); *A61B 90/37* (2016.02); *A61B 90/39* (2016.02); *A61B 2017/00115* (2013.01); *A61B 2017/00119* (2013.01); *A61B 2017/00292* (2013.01); *A61B 2017/00296* (2013.01); *A61B 2017/00349* (2013.01); *A61B 2017/008* (2013.01); *A61B 2017/00809* (2013.01); *A61B 2018/00642* (2013.01); *A61B 2018/00904* (2013.01); *A61B 2034/105* (2016.02); *A61B 2034/2051* (2016.02); *A61B 2090/061* (2016.02); *A61B 2090/0807* (2016.02); *A61B 2090/363* (2016.02); *A61B 2090/364* (2016.02); *A61B 2090/376* (2016.02); *A61B 2090/3904* (2016.02); *A61B 2090/3908* (2016.02); *A61B 2090/3958* (2016.02); *A61B 2090/3987* (2016.02); *A61B 2090/3991* (2016.02); *A61B 2562/0204* (2013.01); *A61B 2562/0233* (2013.01); *A61B 2576/00* (2013.01)

(56) References Cited

U.S. PATENT DOCUMENTS

| | | | |
|---|---|---|---|
| 6,611,700 | B1 | 8/2003 | Vilsmeier et al. |
| 6,836,745 | B2 | 12/2004 | Seller |
| 8,340,379 | B2 | 12/2012 | Razzaque et al. |
| 8,945,147 | B2 | 2/2015 | Ritchey |
| 8,948,845 | B2 | 2/2015 | Glossop |
| 9,770,262 | B2 | 9/2017 | Clancy et al. |
| 9,855,421 | B2 | 1/2018 | Garai et al. |
| 11,058,494 | B2 | 7/2021 | Bueno et al. |
| 11,234,732 | B2 | 2/2022 | Bueno et al. |
| 11,246,666 | B2 | 2/2022 | Bueno et al. |
| 2003/0018246 | A1 | 1/2003 | Govari et al. |
| 2003/0192557 | A1 | 10/2003 | Krag et al. |
| 2004/0059217 | A1 | 3/2004 | Kessman |
| 2006/0253107 | A1 | 11/2006 | Hashimshony |
| 2007/0106152 | A1 | 5/2007 | Kantrowitz |
| 2007/0208250 | A1 | 9/2007 | Sullivan |
| 2008/0077158 | A1 | 3/2008 | Haider |
| 2008/0123927 | A1 | 5/2008 | Miga |
| 2008/0188921 | A1 | 8/2008 | Yamasaki et al. |
| 2009/0221915 | A1 | 9/2009 | Voegele et al. |
| 2009/0226069 | A1 | 9/2009 | Razzaque |
| 2009/0262980 | A1 | 10/2009 | Markowitz et al. |
| 2010/0137845 | A1 | 6/2010 | Ramstein et al. |
| 2010/0137891 | A1 | 6/2010 | Shalon et al. |
| 2011/0021888 | A1 | 1/2011 | Sing et al. |
| 2011/0251607 | A1 | 10/2011 | Kruecker |
| 2011/0313288 | A1 | 12/2011 | Chi Sing et al. |
| 2012/0046521 | A1 | 2/2012 | Hunter et al. |
| 2012/0071824 | A1 | 3/2012 | Chang |
| 2012/0116391 | A1 | 5/2012 | Houser |
| 2013/0113802 | A1 | 5/2013 | Weersink |
| 2013/0317352 | A1 | 11/2013 | Case |
| 2013/0321262 | A1 | 12/2013 | Schecter |
| 2013/0345561 | A1 | 12/2013 | Quigley |
| 2014/0039517 | A1 | 2/2014 | Bowling |
| 2014/0276092 | A1 | 9/2014 | Tenney |
| 2016/0192960 | A1 | 7/2016 | Bueno |
| 2016/0242855 | A1 | 8/2016 | Fichtinger |
| 2018/0256262 | A1 | 9/2018 | Duindam et al. |
| 2019/0183601 | A1 | 6/2019 | Fitelzon et al. |
| 2019/0261886 | A1 | 8/2019 | King et al. |
| 2021/0386449 | A1 | 12/2021 | Bueno et al. |

FOREIGN PATENT DOCUMENTS

| | | |
|---|---|---|
| CN | 104720812 A | 6/2015 |
| CN | 105302974 A | 2/2016 |
| JP | 6654940 B2 | 2/2020 |
| WO | 0108578 A1 | 2/2001 |
| WO | 2005122026 A2 | 12/2005 |
| WO | 2011007312 A1 | 1/2011 |
| WO | 2015109121 A1 | 7/2015 |

OTHER PUBLICATIONS

China National Intellectual Property Administration. Notice on the First Office Action for application 201780029014.8. Mailed on Jan. 4, 2021. With translation. 22 pages.
Angiotech, Breast Localization Needles, Homer Mammalok Gold, http://www.vipemedical.nl/uploadedviper/homemammalock_brochure.pdf?PHPSESSID=7u689s6rh01i9nv50i8mabogq7, date unknown, 1 page.
Ascension Technology Corp., Sensors, http://www.ascension-tech.com/products/sensors/, Copyright 2016, 5 pages.
Cook Medical, Kopans Breast Lesion Localization Needle, https://www.cookmedical.com/products/ir_dkblm_webds/, 2016, 2 pages.
Gill et al., Image-Guided Video Assisted Thoracoscopic Surgery (IVATS)—Phase I-II Clinical Trial, Journal of Surgical Oncology, 2015, 112:18-25.
Northern Digital Inc., Aurora Tools and Sensors, and Accessories, http://www.ndigital.com/medical/products/tools-and-sensors/, Copyright 2016, 7 pages.
Varian Medical Systems, Calypso Extracranial Tracking, https:/www.varian.com/oncology/products/real-time-tracking/calypso-extracranial-tracking, Copyright 1999-2016, 2 pages.
China National Intellectual Property Administration, First Office Action and Search Report, Application No. 201780029014.8, Jan. 4, 2021, 22 pages.
European Patent Office, Extended Search Report, Application No. 14842981.4, Apr. 28, 2017, 9 pages.
European Patent Office, Extended Search Report, Application No. 17764248.5, Oct. 21, 2019, 9 pages.
European Patent Office, Communication Pursuant to Article 94(3) EPC, Application No. 17764248.5, Feb. 17, 2023, 16 pages.
European Patent Office, Extended Search Report, Application No. 20878009.8, Sep. 15, 2023, 11 pages.
PCT International Search Report and Written Opinion, PCT/US2014/054310, Feb. 19, 2015, 19 pages.
PCT International Search Report and Written Opinion, PCT/US2017/021948, Jun. 1, 2017, 15 pages.
PCT International Search Report and Written Opinion, PCT/US2020/056114, Feb. 26, 2021, 31 pages.

(56) References Cited

OTHER PUBLICATIONS

PCT International Search Report and Written Opinion, PCT/US2023/019566, Sep. 21, 2023, 30 pages.
PCT International Search Report and Written Opinion, PCT/US2014/054310, Feb. 19, 2015.
European Patent Office, Extended European Search Report and Search Opinion for application 17764248.5, dated Oct. 21, 2019.
International Search Report with Written Opinion of International Application No. PCT/US2020/056114, mailed Feb. 26, 2021, 31 pages.

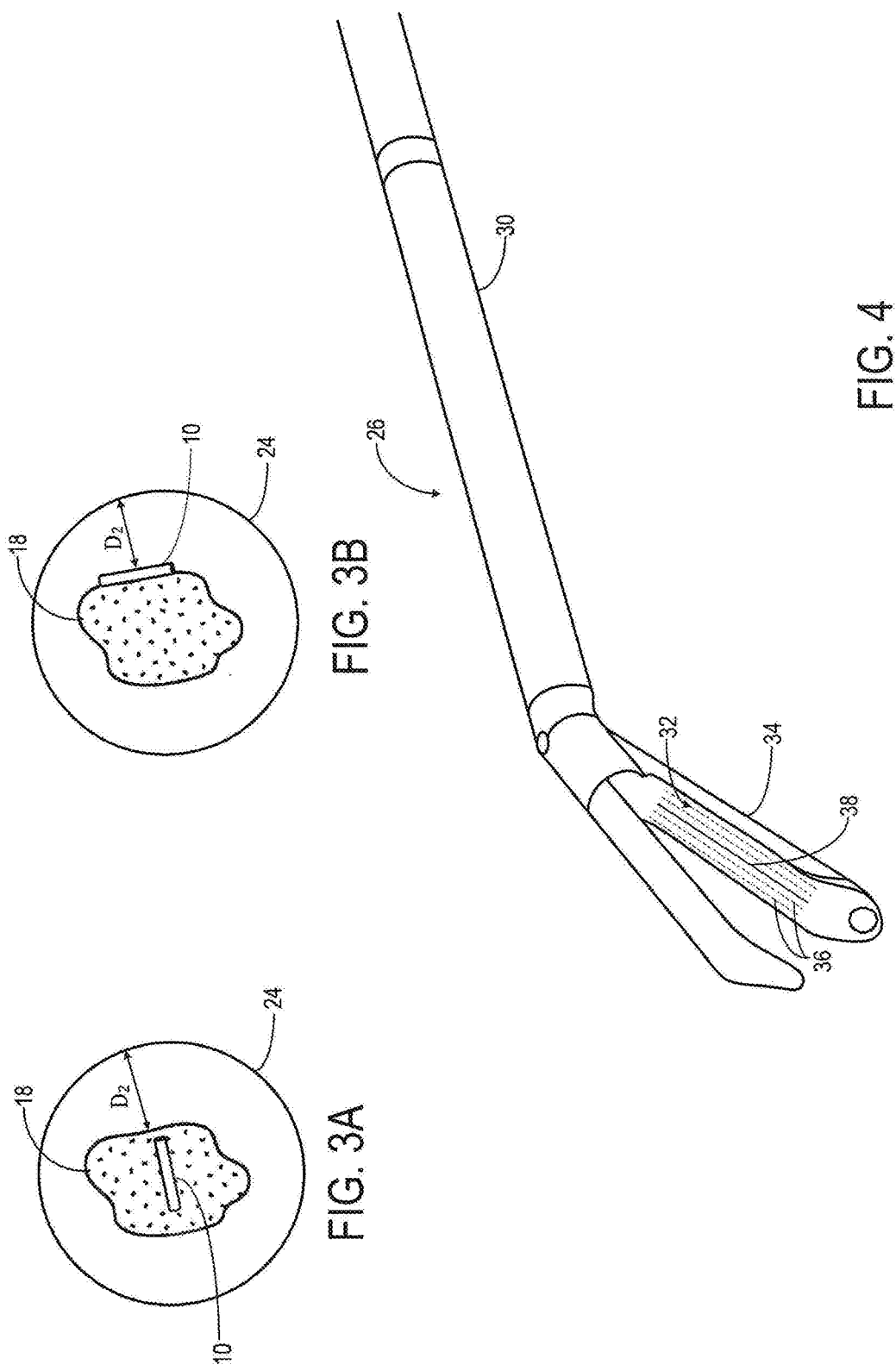

SYSTEM AND METHOD FOR A TISSUE RESECTION MARGIN MEASUREMENT DEVICE

CROSS REFERENCE TO RELATED APPLICATIONS

This application is a continuation of U.S. patent application Ser. No. 15/068,119, filed Mar. 11, 2016, which is a continuation-in-part of application PCT/US2014/054310, filed Sep. 5, 2014, which claims the benefit of the filing date of U.S. provisional patent application Ser. No. 61/874,675 entitled "SYSTEM AND METHOD FOR A TISSUE RESECTION MARGIN MEASUREMENT DEVICE" filed Sep. 6, 2013, the entire contents of which are incorporated by reference herein for all purposes.

STATEMENT REGARDING FEDERALLY SPONSORED RESEARCH

Not Applicable.

BACKGROUND OF THE INVENTION

Minimally invasive surgical resection of tumors involves the precise excision of the tumor while sparing surrounding healthy and critical tissue. Some examples include, but are not limited to, breast conserving surgery and Video-assisted Thoracic Surgery (VATS). Surgical resection of the tumor requires the removal of a margin of tissue around the tumor to ensure complete removal of the tumor cells and improved long-term survival. The default margin is dependent on the type of tumor and micro-invasion of the tumor into the surrounding tissue. Significant deformation of the tissue due to high viscoelasticity or physiological motion (such as collapsing of the lung) can lead to difficulty in localizing the tumor and precise removal of the tumor. As a result, this can lead to tumor recurrence and poor long-term benefits. Two surgical applications are listed below as an example. However, the disclosed system and method may be applied for resection or biopsy of other lesions through a minimally invasive approach or open-surgery.

Current clinical practice to remove lung tissue segments involves opening the chest by cutting the sternum or by spreading the ribs. Many times ribs are broken and often segments are surgically removed during these procedures. The orthopedic trauma alone presents considerable pain and it can complicate the recovery process with patients. Thoracic pain of this magnitude also complicates the task of recovering a patient from general anesthesia since the body acclimates to forced ventilation and the pain can interrupt natural chest rhythm. Patients benefit dramatically from procedures that are performed through small incisions or ports in the chest without causing this orthopedic trauma.

Relatively few thoracic procedures are currently performed using minimally invasive or VATS techniques even though they are well known to provide benefit to the patient by minimizing trauma and speeding recovery times compared to open chest procedures. This is due, at least in part, to the fact that there are only a few available instruments designed specifically to enable thoracic procedures in this way.

Surgery for lung cancer, however, is moving to a minimally invasive approach using VATS and smaller non-anatomic lung resection (i.e., wedge resection) particularly for small lesions. In the conventional method of performing VATS, however, the lung is collapsed leading to difficulty in precisely locating the tumor and determining the resection margins. Additionally, palpation of lung tissue is not possible due to the minimally invasive approach to surgery. Imprecise surgical resection could lead to subsequent tumor recurrence, stressing a critical structure and possibly rupturing the tissue.

Breast conserving surgery (BCS) involves the removal of the tumor while sparing the healthy breast parenchyma around the tumor. Studies have shown that BCS combined with chemotherapy has similar long-term benefits as mastectomy with the additional cosmetic advantage. However, identifying and resecting the entire tumor is a challenging task due to the highly deformable nature of the breast. Achieving the negative surgical margin with minimal damage to the healthy parenchyma is non-trivial due to the soft-tissue nature of the breast.

Therefore, a tissue resection margin measuring device is needed that overcomes the above limitations.

SUMMARY OF THE INVENTION

The present invention relates to a system and method for resecting a tissue mass while compensating for tissue deformation due to its elastic nature and physiologically induced motion. In a non-limiting example, the invention enables minimally invasive surgical procedures by providing a device and method to perform tissue resection that discriminates against traumatizing critical tissue and precisely determines the resection margin. Additionally, auditory, visual and haptic cues may be provided to the surgeon to identify and more precisely measure the tumor margins to ensure complete resection of the tumor.

Some embodiments of the invention provide a system for resecting a tissue mass. The system includes a surgical instrument and a first sensor for measuring a first signal. The first sensor is dimensioned to fit inside or next to (e.g., in close proximity to) the tissue mass. The system also includes a second sensor for measuring a second signal, and the second sensor is coupled to the surgical instrument. A controller is in communication with the first sensor and the second sensor, and the controller executes a stored program to calculate a distance between the first sensor and the second sensor based on the first signal and the second signal.

In some embodiments the system may further include a sleeve dimensioned to engage at least one of a housing of the surgical device and the second sensor. The second sensor may be coupled to the housing of the surgical instrument by an adhesive, for example. The surgical device may be, for example, a stapler, a Bovi pencil or a cutting device configured to cut along a resection margin surrounding the tissue mass, which may be a tumor, a nodule, or a lesion, for example. The resection margin may be included within the distance calculated between the first sensor and the second sensor.

In other embodiments, the first signal received by the first sensor can indicate a position and an orientation of the tissue mass relative to the surgical instrument in real time. Similarly, the second signal received by the second sensor can indicate a position and an orientation of the surgical instrument relative to the tissue mass. In one embodiment, the second sensor indicates a position and an orientation of the surgical instrument in the same reference as the first sensor. The first sensor may be a fiducial marker embedded within an anchor made from superelastic material, and the second sensor may be an instrument sensor. In one embodiment, the first sensor may be configured to measure a position and an orientation of the tissue mass, and the second sensor may be configured to measure a position and an orientation of the surgical instrument.

In one embodiment, the system may further include a third sensor for measuring a third signal. The third sensor may be dimensioned to fit next to the tissue mass at a position opposite the first sensor, such that the third signal received by the third sensor indicates a position and an orientation of the tissue mass relative to the first sensor.

In other embodiments, the first sensor may be embedded within a hook structure. The hook structure may be in the form of a T-bar or J-bar and dimensioned to fit inside a delivery needle and/or a sheath. The delivery needle and/or the sheath may be configured to guide the first sensor, and the hook structure may be configured to anchor the first sensor within the tissue mass. In one embodiment, the first sensor that is embedded within the hook structure may be inserted into the tissue mass under real time image guidance.

In an alternative embodiment, the first sensor is embedded within a hook structure that includes a plurality of prongs, and the first sensor may be dimensioned to fit inside a delivery needle and/or a sheath. The delivery needle and/or the sheath may be configured to guide the first sensor, and the plurality of prongs may be configured to anchor the first sensor within the tissue mass. The hook structure may further comprise a plurality of extensions extending from a tube portion of the hook structure, such that the plurality of extensions may be dimensioned to receive the first sensor.

The system may further include a display in communication with the controller. The display may be coupled to the surgical instrument and configured to display the distance calculated by the stored program executed by the controller. The display may be, but is not limited to, an OLED display or an LCD display. In other embodiments, the system may include an audible source for emitting an audible signal. The audible source may be in communication with the controller, which is configured to execute a stored program to alter the audible signal based on the distance between the first sensor and the second sensor. In one embodiment, the stored program is a navigation system.

The system may further include a piezoelectric actuator coupled to a handle of the surgical instrument. The piezoelectric actuator may be configured to emit a haptic signal. The piezoelectric actuator may be in communication with the controller, which is configured to execute a stored program to alter the haptic signal based on the distance between the first sensor and the second sensor.

The system may further include a monitor for emitting a visual signal in some embodiments. The monitor may be in communication with the controller, the which is configured to execute a stored program to alter the visual signal based on the distance between the first sensor and the second sensor. Additionally or alternatively, the system may include a monitor for displaying a video overlay. The monitor may be in communication with the controller, which is configured to execute a stored program to fuse a laparoscopy image to a virtual endoscopy image to create the video overlay. The video overlay may be configured to identify a position of the tissue mass and the first sensor.

In another embodiment, the invention provides a method for resection of a tissue mass inside a patient. The method includes inserting a first sensor inside or next to the tissue mass (e.g., in close proximity) and capturing at least one image of the first sensor embedded within or next to (e.g., in close proximity to) the tissue mass. A resection margin is calculated around the tissue mass using the at least one image. A surgical instrument inserted into the patient, and the surgical instrument is coupled to a second sensor. The second sensor is tracked relative to the resection margin, and the surgical instrument is used to cut on the resection margin.

In some embodiments the method may further include dimensioning a sleeve to engage at least one of a housing of the surgical device and the second sensor. The second sensor may be coupled to the housing of the surgical instrument by an adhesive, for example. The surgical device may be, for example, a stapler, a Bovi pencil or a cutting device configured to cut along a resection margin surrounding the tissue mass, which may be a tumor, a nodule, or a lesion, for example. The resection margin may be included within the distance calculated between the first sensor and the second sensor.

In other embodiments, the first signal received by the first sensor can indicate a position and an orientation of the tissue mass relative to the surgical instrument in real time. Similarly, the second signal received by the second sensor can indicate a position and an orientation of the surgical instrument relative to the tissue mass. In one embodiment, the second sensor indicates a position and an orientation of the surgical instrument in the same reference as the first sensor. The first sensor may be a fiducial marker constructed from a supereleastic material, and the second sensor may be an instrument sensor. In one embodiment, the first sensor may be configured to measure a position and an orientation of the tissue mass, and the second sensor may be configured to measure a position and an orientation of the surgical instrument.

In one embodiment, the method may further include providing a third sensor for measuring a third signal. The third sensor may be dimensioned to fit next to the tissue mass at a position opposite the first sensor, such that the third signal received by the third sensor indicates a position and an orientation of the tissue mass relative to the first sensor.

In other embodiments, the first sensor may embedded within a hook structure. The hook structure may be in the form of a T-bar or J-bar and dimensioned to fit inside a delivery needle and/or a sheath. The delivery needle and/or the sheath may be configured to guide the first sensor, and the hook structure may be configured to anchor the first sensor within the tissue mass. In one embodiment, the first sensor that is embedded within the hook structure may be inserted into the tissue mass under real time image guidance.

In an alternative embodiment, the first sensor is embedded within a hook structure that includes a plurality of prongs, and the first sensor may be dimensioned to fit inside a delivery needle and/or a sheath. The delivery needle and/or the sheath may be configured to guide the first sensor, and the plurality of prongs may be configured to anchor the first sensor within the tissue mass. The hook structure may further comprise a plurality of extensions extending from a tube portion of the hook structure, such that the plurality of extensions may be dimensioned to receive the first sensor.

The method may further include providing a display in communication with a controller. The display may be coupled to the surgical instrument and configured to display the distance calculated by the stored program executed by the controller. The display may be, but is not limited to, an OLED display or an LCD display. In other embodiments, the method may include emitting an audible signal from an audible source. The audible source may be in communication with the controller, which is configured to execute a stored program to alter the audible signal based on the distance between the first sensor and the second sensor. In one embodiment, the stored program is a navigation method.

The method may further include emitting a haptic signal from a piezoelectric actuator coupled to a handle of the surgical instrument. The piezoelectric actuator may be in communication with the controller, which is configured to execute a stored program to alter the haptic signal based on the distance between the first sensor and the second sensor.

In some embodiments, the method may further include emitting a visual signal on a monitor. The monitor may be in communication with the controller, which is configured to execute a stored program to alter the visual signal based on the distance between the first sensor and the second sensor. Additionally or alternatively, the method may include displaying a video overlay on the monitor. The monitor may be in communication with the controller, which is configured to execute a stored program to fuse a laparoscopy image to a virtual endoscopy image to create the video overlay. The video overlay may be configured to identify a position of the tissue mass and the first sensor.

These and other features, aspects, and advantages of the present invention will become better understood upon consideration of the following detailed description, drawings, and appended claims.

BRIEF DESCRIPTION OF THE DRAWINGS

FIG. 3A is a perspective view of the fiducial sensor embedded in the tissue mass of FIG. 1B with a resection margin surrounding the tissue mass.

FIG. 3B is a perspective view of the fiducial sensor embedded next to the tissue mass of FIG. 1B with the resection margin surrounding the tissue mass.

FIG. 4 is a partial perspective view of a conventional stapler device used for resecting a tissue mass.

DETAILED DESCRIPTION OF THE INVENTION

Figure 1A:
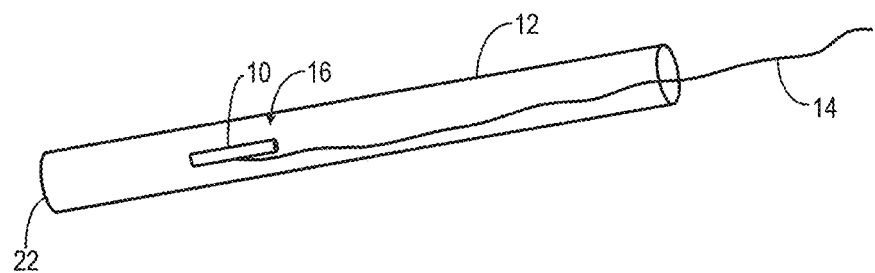
FIG. 1A is a perspective view of an example fiducial sensor being deployed through a delivery needle according to one embodiment of the present invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Figure 1B:
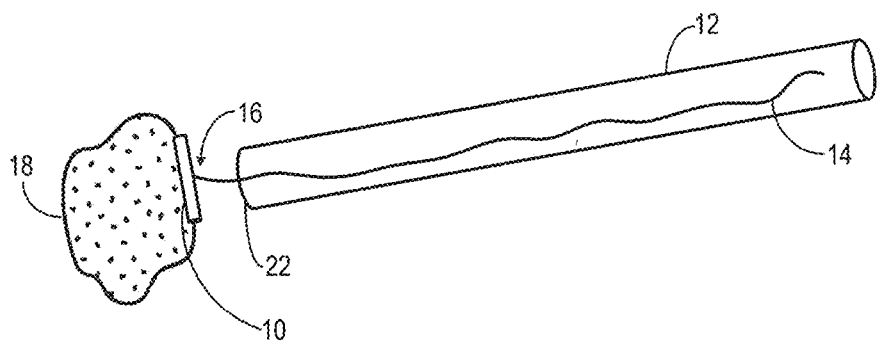
FIG. 1B is a perspective view of the example fiducial sensor of FIG. 1A being deployed through the delivery needle next to a tissue mass according to one embodiment of the present invention.
Figure 1C:
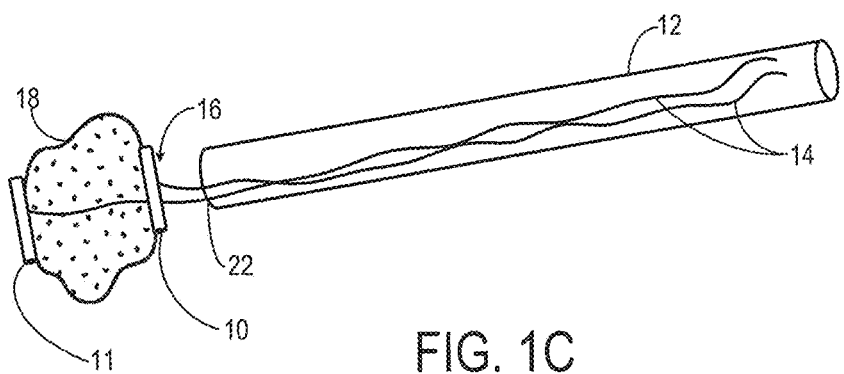
FIG. 1C is a perspective view of an additional fiducial sensor and the example fiducial sensor of FIG. 1A being deployed through the delivery needle next to the tissue mass according to one embodiment of the present invention.

FIGS. 1A-1C illustrate an example fiducial sensor 10 being inserted through a delivery needle 12. The fiducial sensor 10 may be, for example a marker that includes a transmitter that measures position and orientation of a tissue mass 18 in real-time. The fiducial sensor 10 may be attached to a cable 14, as shown in FIGS. 1A-1C, or the fiducial sensor 10 may be wireless. The fiducial sensor 10 may be embedded within a hook structure 16, as shown in FIG. 1A. The hook structure 16 of the fiducial sensor 10 can be made from a superelastic material, for example nitinol or stainless steel, or any other suitable material. This will allow for the fiducial sensor 10 to be inserted through the delivery needle 12 and deployed through an opening 22 (i.e., the lumen) of the delivery needle 12 into the center or the periphery of the tissue mass 18. The tissue mass 18 may be, for example, a tumor, nodule or lesion.

Figure 2:
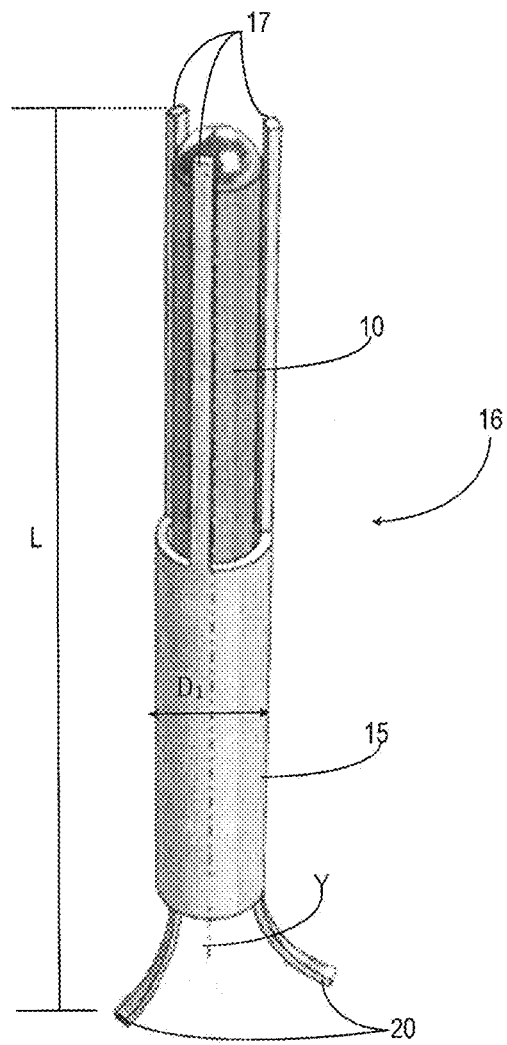
FIG. 2 is a perspective view of an example fiducial sensor embedded within a hook structure according to another embodiment of the present invention.

As shown in FIG. 2, a more detailed view of the fiducial sensor 10 and hook structure 16 is shown. The hook structure 16 may include a tube portion 15 having a plurality of extensions 17 extending from one end of the tube portion 15 and a plurality of prongs 20 extending from an opposing end of the tube portion 15. The tube portion 15 may be, for example, a nitinol tube having an outer diameter $D_1$ between about 0.6 millimeters and about 0.8 millimeters, and the hook structure 16 may have an overall length L between about 8 millimeters and about 12 millimeters. The tube portion 15 may be laser micro-machined into a cylindrical shape having the plurality of extensions 17 extending therefrom to secure the fiducial sensor 10 in place. In some embodiments, the fiducial sensor 10 may be an electromagnetic sensor that is attached to the proximal end of the hook structure 16 using a medical grade epoxy adhesive, such as AA-Bond FDA22.

The plurality of prongs 20, as shown in FIG. 2, may be configured to anchor the hook structure 16, including the fiducial sensor 10, into a tissue mass, such as the tissue mass 18 of FIG. 1B. The plurality of prongs 20 may be constructed from a superelastic shape memory alloy, such as nitinol. The plurality of prongs 20 may be bent, for example, and extend outwardly from a central axis Y of the hook structure 16. The plurality of prongs 20 may also be heat-treated to ensure that the prongs 20 retain the curved shape and the phase structure of the nitinol is in the Martensite phase, for example. In the embodiment shown in FIG. 2, the hook structure 16 includes three prongs 20, however any suitable number of prongs may be provided in order to anchor the hook structure 16 to the tissue mass.

The fiducial sensor 10 along with the hook structure 16 may be inserted through a distal end of the delivery needle 12, which may be an 18-gauge needle, for example. The plurality of prongs 20 of the hook structure 16 may be inserted into the lumen 22 of the delivery needle 12 first. Advantageously, due to the superelastic nature of nitinol, the hook structure 16 can be easily inserted into the lumen 22 of the delivery needle 12. The hook structure 16 may be deployed using a metal stylet (not shown) that is inserted through the lumen 22 of the delivery needle 12. Upon being completely deployed, the plurality of prongs 20 will regain their original curved shape and open up to firmly anchor the hook structure 16 into the tissue mass 18. The delivery needle 12 may then be removed after deployment of the hook structure 16.

In some embodiments, the fiducial sensor 10 along with the hook structure 16 may be inserted through the delivery needle 12 under real-time image guidance (i.e., CT, DynaCT, MRI, Ultrasound, etc.) and embedded within the tissue mass 18, as shown in FIG. 3A, or next to the tissue mass 18 (e.g., in close proximity to), as shown in FIG. 3B. The fiducial sensor 10 may be embedded within or next to the tissue mass 18 before or during a surgical procedure. By using real-time image guidance, the spatial relationship (i.e., position and orientation) of the fiducial sensor 10 to the tissue mass 18 in three dimensions is known at all times. The hook structure 16 may be in the form of a T-bar or J-bar, for example, to anchor the fiducial sensor 10 within or next to the tissue mass 18 to inhibit migration. Advantageously, the force is at the center of the T-bar 16 due to the wire 14, thereby facilitating anchoring the fiducial sensor 10 next to the tissue mass 18. The fiducial sensor 10 embedded within or next to the tissue mass 18 will measure the position and orientation of the tissue mass 18 in real-time in spite of any deformation introduced due to soft tissue deformation or physiological motion such as collapsing of the lung or respiration, for example. Thereby easily identifying the location of the tissue mass 18 that is often difficult to determine.

In an alternative embodiment, shown in FIG. 1C, a second fiducial sensor 11 in the form of a T-bar, for example, may be put in a different location near the tissue mass 18. The second fiducial sensor 11 may have a separate cable 14 from the first fiducial sensor 10, as shown in FIG. 1C, or the first fiducial sensor 10 and the second fiducial sensor 11 may share the same cable 14. The second fiducial sensor 11, or any other such device, can be used to improve the localization of the tissue mass 18, even when there may be deformation. For example, the second fiducial sensor 11 can be placed on the opposite side of the tissue mass 18 from the first fiducial sensor 10 and be recognized by the first fiducial sensor 10 through distortions in the Electromagnetic field. Therefore, by knowing that the tissue mass 18 is between these two sensors, the tissue mass 18 can be localized despite changes in the soft tissue.

Referring now to FIGS. 3A and 3B, once the position and orientation of the tissue mass 18 is known, a resection margin 24 having a predetermined distance $D_2$ surrounding the tissue mass 18 is determined by creating a three dimensional envelope around the tissue mass 18. The resection margin 24 may be manually set to the desired predetermined distance $D_2$, for example two centimeters. The predetermined distance $D_2$ defines a threshold value so when a surgical device 26, described in further detail below, is in a position less than the threshold value auditory, visual and/or haptic cues may be provided to the surgeon or the surgical device 26 to ensure precise and complete resection of the tissue mass 18.

Referring now to FIG. 4, a conventional surgical device 26, such as a surgical stapler, Bovi pencil, kitner laparoscope and/or any suitable cutting, resecting or ablating device, is shown. The surgical device 26 may include a handle 30 coupled to a fastening assembly 32 at an opposite end of the surgical device 26. The fastening assembly 32 may be a single-use component that is removably connected to the handle 30. That is, the fastening assembly 32 may be a cartridge that connects to the handle 30 and is removed after use. The fastening assembly 32 includes a housing 34 that contains a plurality of fasteners 36 that are secured to the tissue during resection of the tissue mass 18. The fastening assembly 32 may also include a blade slot 38 that accommodates a blade (not shown) for cutting along the resection margin 24 of the tissue mass 18.

Figure 5:
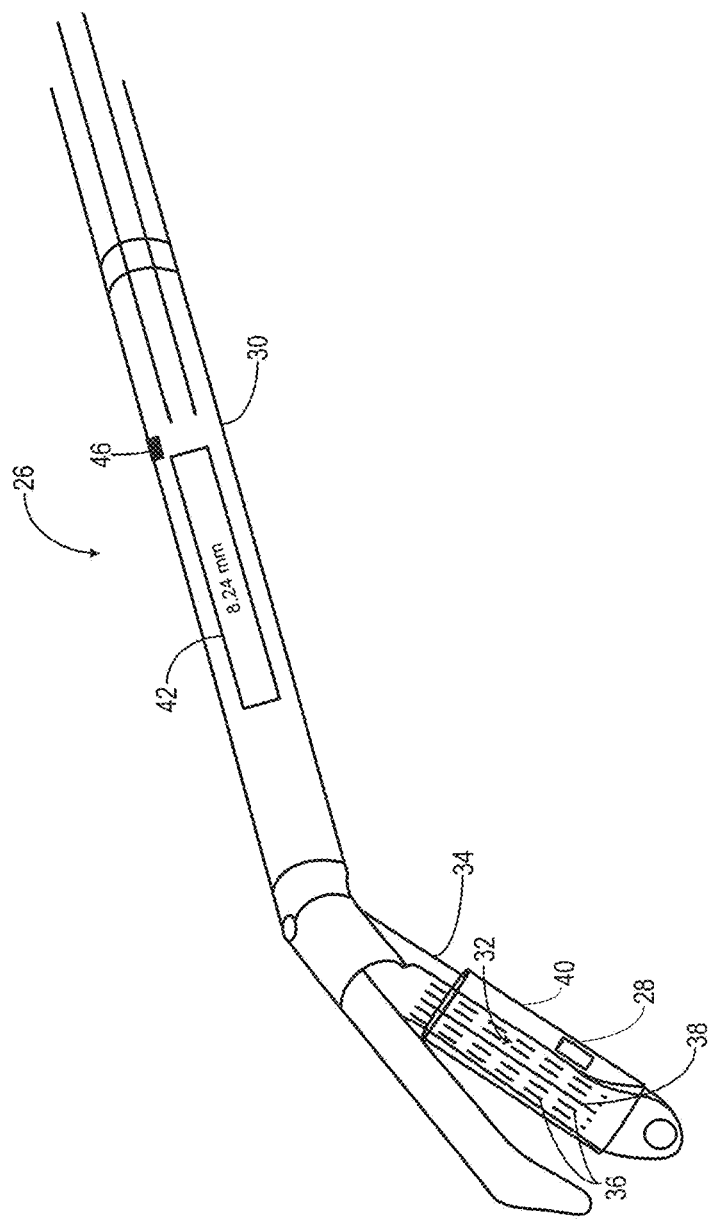
FIG. 5 is a partial perspective view of the stapler device of FIG. 4 with a sleeve including an instrument sensor over a housing of the stapler device according to one embodiment of the present invention.

In a preferred embodiment, the surgical device 26 includes a sleeve 40 that is dimensioned to slide over the housing 34, for example, as shown in FIG. 5. The sleeve 40 may be any commercially available sleeve, for example, that is configured to go over the housing 34 of the surgical device 26. An instrument sensor 28 may be attached, by stitching for example, to the sleeve 40. Alternatively, the instrument sensor 28 may be attached directly to the housing 34 of the surgical device 26 via any suitable adhesive or integrated within the housing 34 itself. Regardless of where the instrument sensor 28 is attached, either the sleeve 40 or the housing 34, the instrument sensor 28 can measure the position and orientation of the surgical device 26 in the same imaging reference frame as the fiducial sensor 10 embedded within or next to the tissue mass 18. In other words, the position of the surgical device 26 may be precisely measured with respect to the fiducial sensor 10 within or next to the tissue mass 18, as will be described in further detail below. Since both the fiducial sensor 10 and the instrument sensor 28 are measured in the same reference frame, errors introduced due to the registration and calibration steps, requiring a change of reference axis, can be minimized.

The sleeve 40 may also include a display 42 that shows the user a distance $D_3$, shown in FIG. 6, of the surgical device 26 from the resection margin 24, as will be described below. The display 42 may be attached to the handle 30 of the surgical device 26 and could be any commercially available organic light-emitting diode (OLED) display or liquid-crystal (LCD) display. In the case of an OLED display, a reformatted CT image of the tissue mass 18 located at the tip of the surgical device 26, for example, may be displayed to the user.

Figure 6:
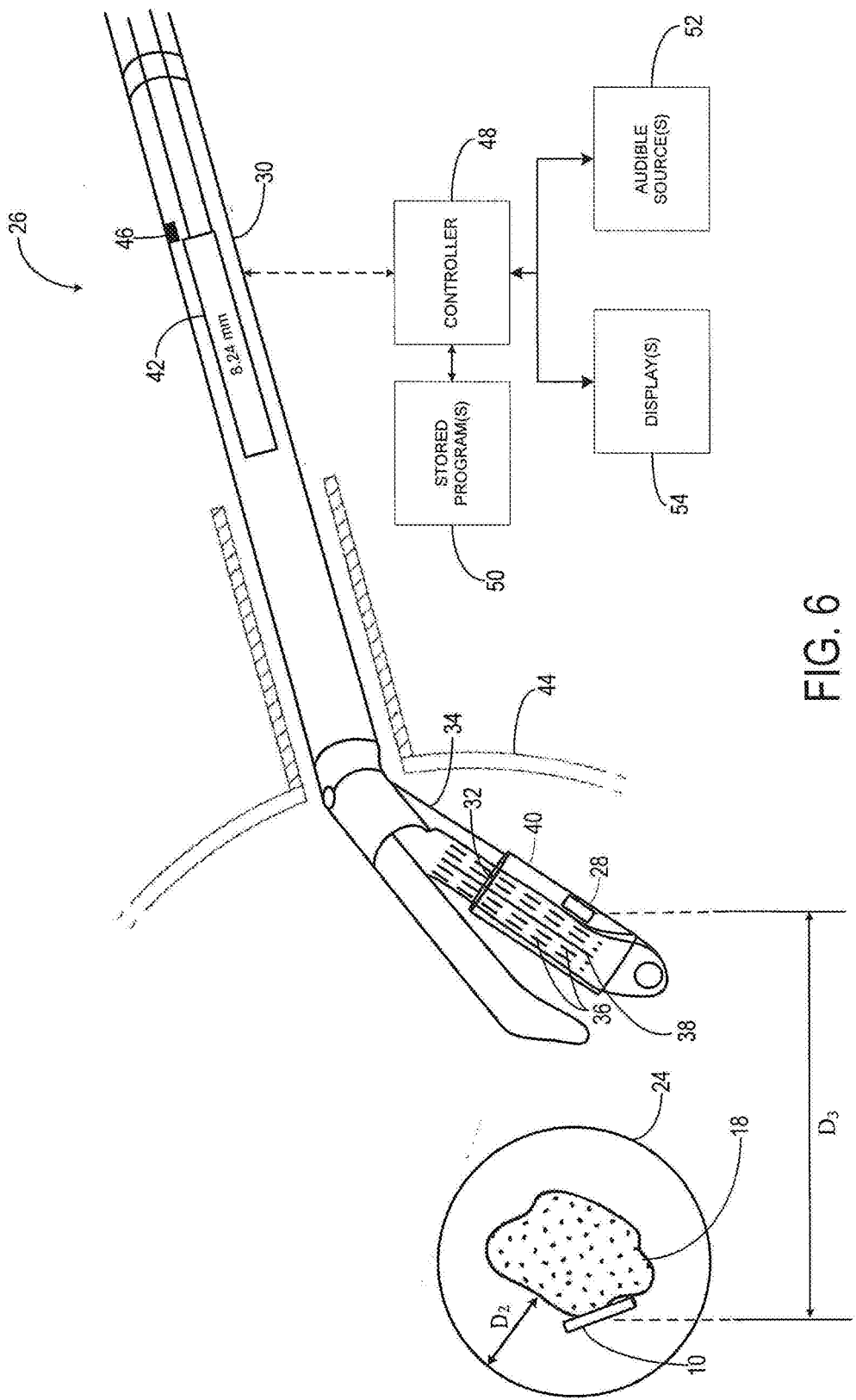
FIG. 6 is a perspective view of the stapler device of FIG. 5 inserted into a patient and shows a distance between the fiducial sensor and the instrument sensor.

Referring now to FIG. 6, during operation, the fiducial sensor 10 is positioned next to or embedded within the tissue mass 18 using the plurality of prongs 20 of the hook structure 16, as previously described. A CT/MRI/fluoroscopic examination, for example, is performed to acquire images of the fiducial sensor 10 embedded within the tissue mass 18. The tissue mass 18 is then segmented from the pre-operative diagnostic CT/MRI examination and a three dimensional model (not shown) of the tissue mass 18 is generated. The intra-operative images obtained during placement of the fiducial sensor 10 may be registered to the patient's diagnostic exam, and the location of the fiducial sensor 10 may be estimated. As previously discussed, the resection margin 24 having the predetermined distance $D_2$ surrounding the tissue mass 18 is displayed to the user on a monitor (not shown) as a three dimensional envelope or proximity sphere around the tissue mass 18. The predetermined distance $D_2$ of the resection margin 24 may be determined based on the surgeon's preferences and the type of tissue mass 18.

The surgical device 26 is then inserted into a body 44 (i.e., the patient), as shown in FIG. 6, to cut the tissue mass 18 along the resection margin 24. The fiducial sensor 10 embedded within or close to the tissue mass 18 is in electrical or wireless communication with a controller 48. The controller 48 may be a programmable logic controller (PLC) and is configured to interpret a signal generated by the fiducial sensor 10. The fiducial sensor 10 may be an electromagnetic sensor, for example, that generates a signal proportional to the position and orientation (e.g., a GPS coordinate) of the fiducial sensor 10. The signal generated by the fiducial sensor 10 may be for example an electrical signal and the controller 48 may interpret this signal via a stored program 50. The stored program 50 may include, for example a navigation system that is in communication with the fiducial sensor 10 and the instrument sensor 28.

Similarly, the instrument sensor 28 may be an electromagnetic sensor, for example, that generates a signal proportional to the position and orientation (e.g., a GPS coordinate) of the instrument sensor 28. The signal generated by the instrument sensor 28 may be, for example, an electrical signal and the controller 48 may interpret this signal via a stored program 50. The fiducial sensor 10 and the instrument sensor 28 communicate with the controller 48 and relay the position and orientation of the tissue mass 18 and the surgical device 26 using the navigation system. In some embodiments, the stored program 50 may be configured to run calibration and/or registration algorithms to track the distal tip of the surgical device 26 and the normal vector to the surgical device 26. Thereafter, the stored program 50 of the controller 48 calculates the distance $D_3$, shown in FIG. 6, between the fiducial sensor 10 and the instrument sensor 28 such that when the surgical device 26 is below a threshold value of $D_3$, an auditory, visual or haptic cue is generated for the user.

As the surgical device 26 is navigated towards the resection margin 24 of the tissue mass 18, the surgical device 26 may excise the tissue mass 18 while minimizing damage to surrounding tissue due to both the fiducial sensor 10 and instrument sensor 28 being actively tracked. Minimal damage to the surrounding healthy tissue may also ensure normal physiological function, for example lung function. Utilizing feedback from the fiducial sensor 10 and the instrument sensor 28 on the surgical device 26, the distance $D_3$ from the tissue mass 18 and the surgical device 26 may be known to the user and visible on the display 42 at all times. As a result, the desired resection margin 24 may be maintained at all times, thereby ensuring complete resection of the tissue mass 18. In an alternative embodiment, the position and orientation data of the tissue mass 18 and the surgical device 26 may lock or unlock the surgical device 26 to inhibit erroneous resection of the tissue mass 18.

In some embodiments, the stored program 50 of the controller 48 may be configured to include one or more deformation algorithm that estimates or models changes that can occur to the resection margin 24 during operation, as a result of deformations of the tissue mass 18 and/or the surrounding tissue. The deformation algorithms attempt to account for any such changes to the resection margin 24 to provide more accurate resection margins to a user during operation, which aids in complete resection of the tissue mass 18 while limiting damage to, or removal of, healthy, surrounding tissue.

In one non-limiting example, the stored program 50 includes a deformation algorithm that assumes that the tissue mass 18 (e.g., a breast tumor) is rigid and that the surrounding tissue (e.g., the parenchyma) deforms. The algorithm assumes every point on the tissue mass 18 moves along with the fiducial sensor 10, which is anchored to the tissue mass 18 as described above. In another non-limiting example, the stored program 50 includes a deformation algorithm that assumes the tissue mass 18 is a rigid object moving through a viscoelastic or fluid medium. In yet another non-limiting example, patient specific properties of the tissue mass 18 and the surrounding tissue can be measured, for example, via a CT/MRI/fluoroscopic examination, to predict deformations to tissue mass 18 that occur during an operation for that specific patient. It should be appreciated that the deformation algorithms of the stored program 50 may operate on a real-time basis with the navigation system of the stored program 50.

More specifically, a tissue mass 18 (e.g., a tumor) can be segmented from volumetric images obtained, for example, from the CT/MRI/fluoroscopic examination, to create a surface model. Based upon a default resection margin inputted into the navigation system by a user, a segmented tumor label map can be dilated to the desired resection margin to create a surface model corresponding to the resection margin. Due to deformation of the tumor and the surrounding tissue, the resection margin can change, for example, due to movement of the patient. A linear elastic volumetric finite element model ("FEM") mesh can therefore be created from the surface model of the tumor and the resection margin. Using the FEM model, an estimate of the displacement of the other nodes of tissue mass 18 can be made, given the real-time position measurement of the fiducial sensor 10. Stiffness values may not be entirely accurate for the FEM model, and the FEM model may be constrained in one example to the tissue mass 18 and the surrounding tissue. Uncertainty measurements of the tissue mass 18 and the surrounding tissue deformation can therefore be provided to a user in real-time based upon the uncertainty in the estimated stiffness values of the FEM mesh.

As described above, auditory, visual and haptic cues may be provided to the surgeon and/or the surgical device 26 to identify the resection margin 24 to ensure precise and complete resection of the tissue mass 18. For example, an audible source 52 may be configured to emit an audible signal. The audible source 52 may be in communication with the controller 48 that is configured to execute the stored program 50 to alter the audible signal based on the distance $D_3$ between the instrument sensor 28 and the fiducial sensor 10. The instrument sensor 28 uses the signal generated by the fiducial sensor 10 to enable the controller 48 to execute the stored program 50 to calculate the distance $D_3$, shown in FIG. 6, between the fiducial sensor 10 and the instrument sensor 28 such that when the surgical device 26 is below a threshold value of $D_3$, the audible signal is generated. The audible signal may be, for example a tone, beep or alarm. The audible signal may also increase in frequency or duty cycle as the distance $D_3$ decreases, such that as the surgical device 26 is navigated too close to the resection margin 24, the audible signal's frequency or duty cycle increases.

In addition to the auditory cues, visual cues may also be provided to the user on one or more displays 54 in communication with the controller 48. The one or more displays 54 may include, for example, on an endoscopic display or a separate monitor. For example, the endoscopic display or the separate monitor may be configured to emit a visual signal. The endoscopic display or the separate monitor may be in communication with the controller 48 that is configured to execute a stored program 50 to alter the visible signal based on the distance $D_3$ between the instrument sensor 28 and the fiducial sensor 10. The instrument sensor 28 uses the signal generated by the fiducial sensor 10 to enable the controller 48 to execute the stored program 50 to calculate the distance $D_3$, shown in FIG. 6, between the fiducial sensor 10 and the instrument sensor 28 (e.g., near the tip of the surgical device 26), and/or between the instrument sensor 28 (e.g., near the tip of the surgical device 26) and a vector normal to the hook structure 16, such that when the surgical device 26 is below a threshold value of $D_3$, the visual signal is generated. The visual signal may be, for example a solid or flashing light shown on the one or more displays 54, such as the endoscopic display or the separate monitor. The visual signal may also increase in frequency or brightness, for example, as the distance $D_3$ decreases, such that as the surgical device 26 is navigated too close to the resection margin 24, the visual signal's frequency and/or brightness increases.

In one non-limiting example, the visual cue may be shown as a color changing sphere, for example, on one of the displays 54. The color changing sphere may be representative of the tissue resection margin 24, for example, such that the color changes based on the distance $D_3$ between the instrument sensor 28 and the fiducial sensor 10. Thus, as the instrument sensor 28 approaches the fiducial sensor 10, for example, the sphere may be shown in the display 54 in a first color. Likewise, as the instrument sensor 28 moves away from the fiducial sensor 10, the sphere may be shown on the display 54 in a second color, for example, thereby allowing the surgeon to determine, visually, the distance $D_3$ between the instrument sensor 28 and the fiducial sensor 10.

Figure 7B:
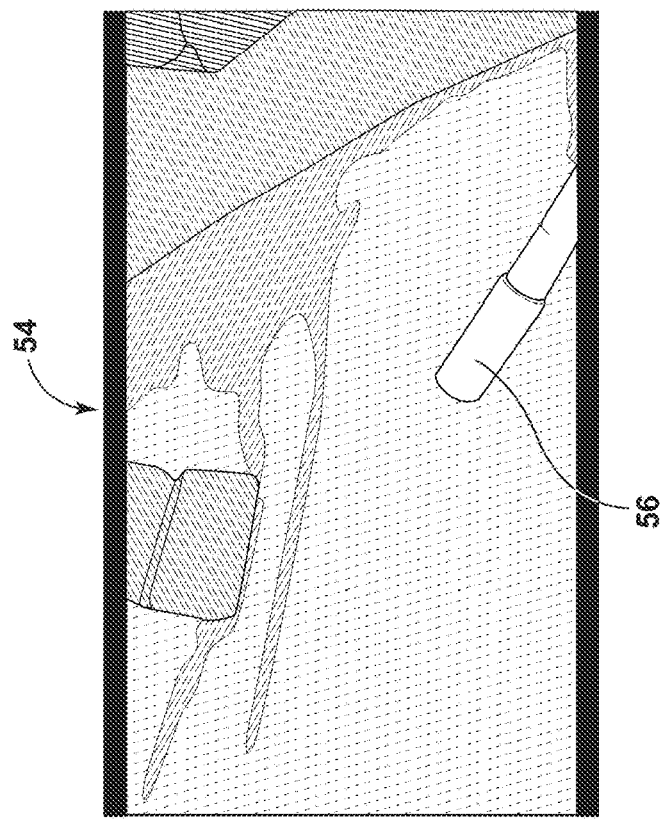
FIG. 7B is an example screenshot of a laparoscopy view of the tissue mass.
Figure 7A:
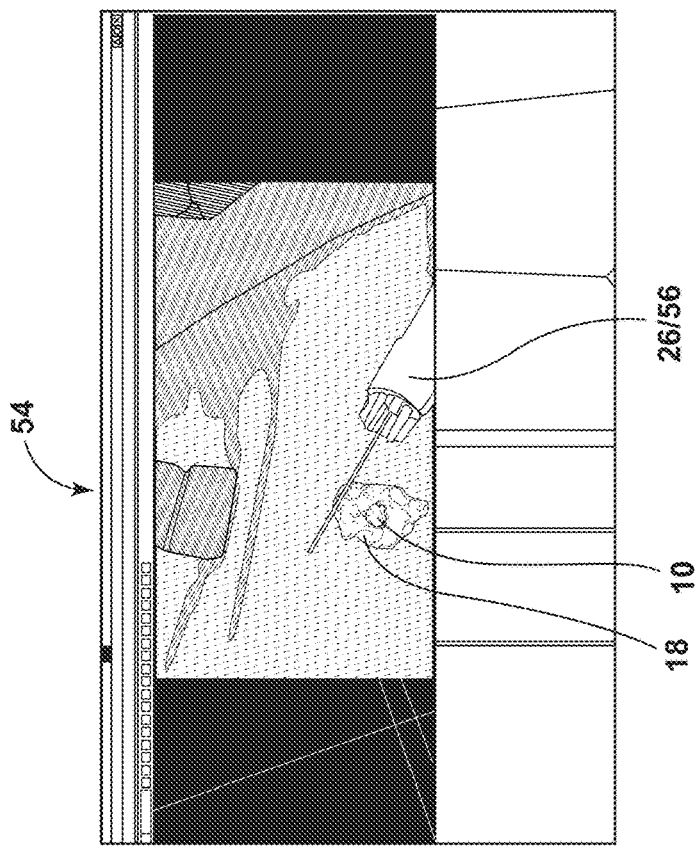
FIG. 7A is an example screenshot of a virtual endoscopy view of the tissue mass overlaid on a laparoscopy view.

Although quantitative, visual, and auditory cues may be provided to the clinician to identify the distance of the resection margin 24 from the surgical instrument 26, the visual cue may further include a video overlay provided to the user on one or more of the displays 54 in communication with the controller 48. For example, a video overlay may be implemented to fuse the laparoscopy images and virtual endoscopy images to confirm the position of the fiducial sensor 10 and the tissue mass 18, as shown on the display 54 of FIG. 7A. Based on the position of the laparoscope 56, as shown on the display 54 of FIG. 7B, the virtual endoscopy video of the three dimensional anatomy can be generated. The focal length and field of view may be input to control the virtual endoscopy view generated using a visualization toolkit camera, for example, of the three dimensional view.

Haptic cues may also be provided to the user on the surgical device 26. For example, a piezoelectric actuator 46 may be attached to the handle 30 of the surgical device 26 that is configured to emit a haptic signal. The piezoelectric actuator 46 may be in electrical communication with the controller that is configured to execute a stored program to alter the haptic signal based on the distance $D_3$ between the instrument sensor 28 and the fiducial sensor 10. The instrument sensor 28 uses the signal generated by the fiducial sensor 10 to enable the controller to execute the stored program to calculate the distance $D_3$, shown in FIG. 6, between the fiducial sensor 10 and the instrument sensor 28 such that when the surgical device 26 is below a threshold value of $D_3$, the haptic signal is generated. The haptic signal may be, for example a vibration applied to the handle 30 of the surgical device 26. The haptic signal may also increase in amplitude and/or frequency, for example, as the distance $D_3$ decreases, such that as the surgical device 26 is navigated too close to the resection margin 24, the haptic signal's amplitude and/or frequency increases.

Although the above described system and method for resecting a tissue mass was described for the surgery involving the lung, it is also applicable to resection of tumor or other non-tumor lesions in any other organ or structure of the body, for example resection for breast conserving surgery, sarcoma resection, partial nephrectomy or lung wedge resection surgery. In addition, the above described system and method for resecting a tissue mass is not limited to VATS or minimally invasive surgery.

What is claimed is:

1. A system for resecting a target tissue mass from a host tissue mass, wherein the host tissue mass is deformable, the system comprising:
   a surgical instrument;
   a first fiducial sensor, dimensioned to fit at least one of inside of and next to the target tissue mass, the first fiducial sensor including a hook to anchor the first fiducial sensor at least one of inside of and next to the target tissue mass so that the first fiducial sensor remains in known spatial relation to the target tissue mass, the first fiducial sensor adapted to measure position of the first fiducial sensor within a first frame of reference;
   a second fiducial sensor, coupled to the surgical instrument, the second fiducial sensor adapted to measure position of the second fiducial sensor within the first frame of reference; and
   a controller in communication with the first fiducial sensor and the second fiducial sensor, the controller being configured to:
   receive a three-dimensional tissue mass model and a three-dimensional virtual margin model;
   register the position of the first fiducial sensor, the second fiducial sensor, the three-dimensional tissue mass model, and the three-dimensional virtual margin model in a common frame of reference;
   update, in real-time, the position of the implantable fiducial sensor, the three-dimensional tissue mass model, and the three-dimensional virtual margin model in the common frame of reference based on the measured position of the first implantable sensor within the first frame of reference;
   update, in real-time, the position of the second fiducial sensor in the common frame of reference based on the measured position of the second fiducial sensor within the first frame of reference,
   such that the positions of the three-dimensional tissue mass model, the three-dimensional virtual margin model, and the instrument fiducial sensor are determined relative to one another regardless of deformation of the host tissue mass.

2. The system of claim 1, further comprising:
   a sleeve dimensioned to engage at least one of a housing of the surgical instrument and the second fiducial sensor.

3. The system of claim 1, wherein the first fiducial sensor is adapted to measure the position and orientation of the first fiducial sensor within the first frame of reference, wherein the second fiducial sensor is adapted to measure the position and orientation of the second fiducial sensor within the first frame of reference, the controller being further configured to: register the position and orientation of the first fiducial sensor, the second fiducial sensor, the three-dimensional tissue mass model, and the three-dimensional virtual margin model in the common frame of reference; update, in real-time, the position and orientation of the implantable fiducial sensor, the three-dimensional tissue mass model, and the three-dimensional virtual margin model in the common frame of reference based on the measured position and orientation of the first implantable sensor within the first frame of reference; update, in real-time, the position and orientation of the second fiducial sensor in the common frame of reference based on the measured position and orientation of the second fiducial sensor within the first frame of reference, such that the positions and orientations of the three-dimensional tissue mass model, the three-dimensional virtual margin model, and the instrument fiducial sensor are determined relative to one another regardless of deformation of the host tissue mass.

4. The system of claim 1, wherein the hook is in the form of a T-bar and is dimensioned to fit inside at least one of a delivery needle and a sheath;
wherein the at least one of the delivery needle and the sheath is configured to guide the first fiducial sensor.

5. The system of claim 4, wherein the first fiducial sensor including the hook is inserted into the tissue mass under real time image guidance.

6. The system of claim 1, wherein the hook includes a plurality of prongs and is dimensioned to fit inside at least one of a delivery needle and a sheath;
wherein the at least one of the delivery needle and the sheath is configured to guide the first fiducial sensor.

7. The system of claim 6, wherein the hook further comprises a plurality of extensions extending from a tube portion of the hook, the plurality of extensions dimensioned to receive the first fiducial sensor.

8. The system of claim 1, wherein the first fiducial sensor comprises a superelastic material.

9. The system of claim 1, wherein the target tissue mass is at least one of a tumor, a nodule and a lesion.

10. The system of claim 1, wherein the surgical instrument is at least one of a stapler, Bovi pencil and a cutting device.

11. The system of claim 1, further comprising:
a display in communication with the controller.

12. The system of claim 11, wherein the display is at least one of an OLED and LCD display.

13. The system of claim 1, further comprising:
an audible source for emitting an audible signal, the audible source being in communication with the controller, the controller configured to alter the audible signal based on a distance between the second fiducial sensor and the three-dimensional virtual margin model.

14. The system of claim 1, further comprising:
a piezoelectric actuator for emitting a haptic signal, the piezoelectric actuator being in communication with the controller, the controller configured to alter the haptic signal based on a distance between the second fiducial sensor and the three-dimensional virtual margin model.

15. The system of claim 14, wherein the piezoelectric actuator is coupled to a handle of the surgical instrument.

16. The system of claim 1, further comprising:
a monitor for emitting a visual signal, the monitor in communication with the controller, the controller configured to alter the visual signal based on the positions of the three-dimensional virtual margin model and the second fiducial sensor.

17. The system of claim 1, further comprising:
a monitor for displaying a video overlay, the monitor in communication with the controller, the controller configured to execute a stored program to fuse a laparoscopy image to a virtual endoscopy image to create the video overlay.

18. The system of claim 1, wherein the controller executes a stored program including a navigation system.

19. The system of claim 1, wherein the controller executes a stored program including a deformation algorithm.

20. The system of claim 1, wherein the second sensor is coupled to a housing of the surgical instrument by an adhesive.

21. The system of claim 1, further comprising a third fiducial sensor dimensioned to fit next to the target tissue mass at a position opposite the first sensor, the third fiducial sensor adapted to measure position of the third fiducial sensor within the first frame of reference.

22. A method for resection of a target tissue mass from a host tissue mass inside a patient, wherein the host tissue mass is deformable, the method comprising:
(a) anchoring a first fiducial sensor at least one of inside and next to the target tissue mass so that the first fiducial sensor remains in known spatial relation to the target tissue mass, the first fiducial sensor adapted to measure position of the first fiducial sensor within a first frame of reference;
(b) inserting a surgical instrument into the patient, the surgical instrument coupled to a second fiducial sensor, the second fiducial sensor adapted to measure position of the second fiducial sensor within the first frame of reference;
(c) receive a three-dimensional tissue mass model and a three-dimensional virtual margin model,
(d) register the position of the first fiducial sensor, the second fiducial sensor, the three-dimensional tissue mass model, and the three-dimensional virtual margin model in a common frame of reference;
(e) update, in real-time, the position of the implantable fiducial sensor, the three-dimensional tissue mass model, and the three-dimensional virtual margin model in the common frame of reference based on the measured position of the first implantable sensor within the first frame of reference; and
(f) update, in real-time, the position of the second fiducial sensor in the common frame of reference based on the measured position of the second fiducial sensor within the first frame of reference,
such that the positions of the three-dimensional tissue mass model, the three-dimensional virtual margin model, and the instrument fiducial sensor are determined relative to one another regardless of deformation of the host tissue mass.

* * * * *